United States Patent [19]

Boschelli et al.

[11] Patent Number: 4,962,119

[45] Date of Patent: Oct. 9, 1990

[54] TRIAZOLE DERIVATIVES OF FENAMATES AS ANTIINFLAMMATORY AGENTS

[75] Inventors: Diane H. Boschelli, Novi; David T. Connor, Ann Arbor, both of Mich.; Daniel L. Flynn, Mundelein, Ill.; Jagadish C. Sircar; Milton L. Hoefle, both of Ann Arbor, Mich.

[73] Assignee: Warner-Lambert Company, Morris Plains, N.J.

[21] Appl. No.: 364,345

[22] Filed: Jun. 9, 1989

[51] Int. Cl.$^5$ .................. A61K 31/41; C07D 249/12; C07D 249/14
[52] U.S. Cl. .................. 514/384; 514/383; 548/262.6; 548/263.2; 548/264.8; 548/265.4; 548/265.6; 548/266.8; 548/267.2; 548/267.8; 548/268.6
[58] Field of Search .................. 514/383, 384; 548/262.6, 263.2, 264.8, 265.4, 265.6, 266.8, 267.2, 267.8, 268.6

[56] References Cited

U.S. PATENT DOCUMENTS 4,618,617 10/1986 Yamamoto .................. 514/364

OTHER PUBLICATIONS

Chemical Abstracts—J6 1005-072-A Sumitomo Chem Ind KK.
Legrand et al., "Heterocyclic Sulfur Compounds, etc." CA 84:17262u (1976).

*Primary Examiner*—Glennon H. Hollrah
*Assistant Examiner*—Patricia L. Morris
*Attorney, Agent, or Firm*—Joan Thierstein

[57] ABSTRACT

The present invention is novel compounds which are 1,2,4-triazoles, derivatives of fenamates and pharmaceutically acceptable additions and base salts thereof, pharmaceutical compositions and methods of use thereof. The invention compounds are now found to have activity as inhibitors of 5-lipoxygenase and/or cyclooxygenase providing treatment of conditions advantageously affected by such inhibition including inflammation, arthritis, pain, fever, and the like.

9 Claims, No Drawings

TRIAZOLE DERIVATIVES OF FENAMATES AS ANTIINFLAMMATORY AGENTS

BACKGROUND OF THE INVENTION

The present invention is novel compounds which are triazole derivatives of fenamates, and pharmaceutically acceptable acid addition or base salts thereof, pharmaceutical compositions and methods of use therefor. The invention compounds are now found to have activity as inhibitors of 5-lipoxygenase and/or cyclooxygenase providing treatment of conditions advantageously affected by such inhibition including inflammation, arthritis, pain, fever, and the like. Thus, the present invention is also a pharmaceutical composition or method of use therefor.

Copending application PD-3710 and PD-3862 disclose various derivatives of fenamates but having no triazole substituents. PD-3715 discloses triazole ring systems which are derivatives of 2,6-ditertiarybutylphenol.

Thus, the differences between the present invention and the teachings of the references are readily apparent.

SUMMARY OF THE INVENTION

The present invention is a compound of the formula (I)

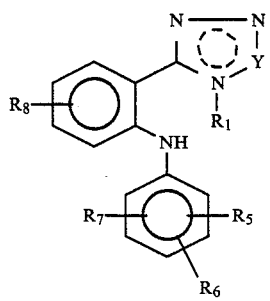

and pharmaceutically acceptable salts thereof; wherein
$R_1$ is hydrogen or lower alkyl;
Y is (1) C-SR$_1$ wherein $R_1$ is independently as defined above, (2)

wherein $R_2$ is lower alkyl, (3)

wherein $R_2$ is independently as defined above, (4) C-NR$_1$R$_3$ wherein $R_1$ is independently as defined above and $R_3$ is hydrogen or lower alkyl, (5) COR$_1$ wherein $R_1$ is independently as defined above, (6) CR$_4$ wherein R$_4$ is hydrogen, lower alkyl, halogen, CF$_3$, CO$_2$R$_1$, or

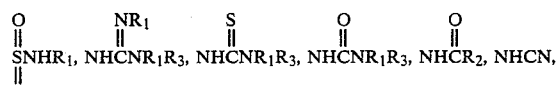

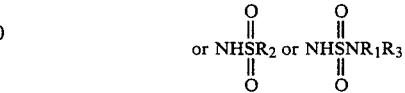

wherein $R_1$, $R_2$, and $R_3$ are independently as defined above; and
$R_5$, $R_6$, $R_7$, and $R_8$ are independently hydrogen, fluoro, chloro, bromo, iodo, trifluoromethyl-, lower alkyl, CN, hydroxy, lower alkoxy, —S(O)n-lower alkyl, NO$_2$, or NR$_9$R$_{10}$ wherein R$_9$ or R$_{10}$ are independently H, lower alkyl or acyl; and n is an integer of 0 through 2.

The present invention is also a pharmaceutical composition for the treatment of conditions advantageously affected by the inhibition of 5-lipoxygenase and/or cyclooxygenase which comprises an amount, effective for the treatment of the condition, of a compound of the formula I and the pharmaceutically acceptable acid addition or base salt thereof together with a pharmaceutically acceptable carrier. The condition is meant to include, for example, arthritis or other inflammatory diseases, allergic diseases, pain, fever, and psoriasis, but preferably inflammatory diseases.

The present invention is also a method for treatment of the condition as noted above in a mammal, including humans, suffering therefrom with a compound of the formula I or the pharmaceutically acceptable acid addition or base salt thereof, in unit dosage form The invention also provides for use of any such compound of formula I or salt thereof in the manufacture of medical therapeutical agents.

Pharmaceutical composition or use of the compound or salt of formula I is meant to include treatment understood to be prophylactic pertinent to the foregoing named condition.

The preferred compound of the formula I in the present invention is:

5-[2-[(3-trifluoromethylphenyl)amino]phenyl]-2,4-dihydro-3H-1,2,4-triazole-3-thione.

DETAILED DESCRIPTION OF THE INVENTION

In the compounds of formula (I) the term "lower alkyl" includes an alkyl group of from one to six carbons such as methyl, ethyl, propyl, butyl, and the like and isomers thereof. Halogen is chloro, bromo or fluoro. Lower alkoxy includes from one to six carbons and therefore includes methoxy, ethoxy, propoxy, butoxy and the like and isomers thereof Acyl is of from two to six carbons and thus includes acetyl, propionyl, butyryl, and the like and isomers thereof.

The compounds of the formula I may exist as tautomers which are readily determined from art recognized tautomerism. Such tautomers are, for example, represented by $I_a' \rightleftharpoons I_b'$ as follows:

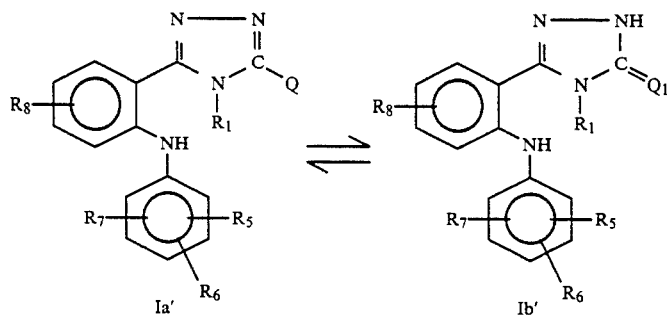

wherein Q is SH, OH or NH$_2$ and Q$_1$ is S, O or NH.

Appropriate compounds of formula I are useful in the free base form, in the form of base salts where possible, and in the form of acid addition salts The three forms are within the scope of the invention. In practice, use of the salt form amounts to use of the base form. Pharmaceutically acceptable salts within the scope of the invention may be those derived from mineral acids such as hydrochloric acid and sulfuric acid; and organic acids such as ethanesulfonic acid, benzenesulfonic acid, p-toluenesulfonic acid, and the like, giving the hydrochloride, sulfamate, ethanesulfonate, benzenesulfonate, p-toluenesulfonate and the like, respectively, or those derived from bases such as suitable organic and inorganic bases. Examples of pharmaceutically acceptable base addition salts with compounds of the present invention include organic bases which are nontoxic and strong enough to form such salts. These organic bases form a class whose limits are readily understood by those skilled in the art. Merely for purposes of illustration, the class may be said to include mono-, di-, and trialkylamines such as methylamine, dimethylamine, and triethylamine; mono-, di-, or trihydroxyalkylamines such as mono-, di-, or triethanolamine; amino acids such as arginine and lysine; guanidine; N-methylglucosamine; N-methylglucamine; L-glutamine; N-methylpiperazine; morpholine; ethylenediamine; N-benzylphenethylamine; tris(hydroxymethyl)aminomethane; and the like. (See for example, "Pharmaceutical Salts," *J. Pharm. Sci.*, 66(1):1–19 (1977).) Salts of inorganic bases include sodium, potassium, calcium or the like.

The acid addition salts of said basic compounds are prepared either by dissolving the free base or acid of compound I in aqueous or aqueous alcohol solution or other suitable solvents containing the appropriate acid or base and isolating the salt by evaporating the solution, or by reacting the free base of compound I with an acid as well as reacting compound I having an acid group thereon with a base such that the reactions are in an organic solvent, in which case the salt separates directly or can be obtained by concentration of the solution. Salts can also be prepared by adding base to an aqueous alcohol solution of another salt.

The compounds of the invention may contain geometric isomers. Thus, the invention includes the individual isomers and mixtures thereof. The individual isomers may be prepared or isolated by methods known in the art.

In determining when a lipoxygenase, cyclooxygenase, or dual lipoxygenase/cyclooxygenase inhibitor is indicated, of course inter alia, the particular condition in question and its severity, as well as the age, sex, weight, and the like of the subject to be treated, must be taken into consideration and this determination is within the skill of the attendant physician.

For medical use, the amount required of a compound of formula I or pharmacologically acceptable salt thereof to achieve a therapeutic effect will, of course, vary both with the particular compound, the route of administration, the mammal under treatment, and the particular disorder or disease concerned. A suitable dose of a compound of formula I or pharmacologically acceptable salt thereof for a mammal suffering from, or likely to suffer from any condition as described hereinbefore is 0.1 μg–500 mg of the compound per kilogram body weight. In the case of systemic administration, the dose may be in the range of 0.5 to 500 mg of the compound per kilogram body weight, the most preferred dosage being 0.5 50 mg/kg of mammal body weight administered two or three times daily. In the case of topical administration, e.g., to the skin or eye, a suitable dose may be in the range 0.1 ng–100 μg of the compound per kilogram, typically about 0.1 μg/kg.

In the case of oral dosing for the treatment or prophylaxis of arthritis or inflammation in general, due to any course, a suitable dose of a compound of formula I or physiologically acceptable salt thereof, may be as specified in the preceding paragraph, but most preferably is from 1 mg to 10 mg of the compound per kilogram, the most preferred dosage being from 1 mg to 5 mg/kg of mammal body weight, for example from 1 to 2 mg/kg.

It is understood that the ordinarily skilled physician or veterinarian will readily determine and prescribe the effective amount of the compound to prevent or arrest the progress of the condition for which treatment is administered. In so proceeding, the physician or veterinarian could employ relatively low doses at first, subsequently increasing the dose until a maximum response is obtained.

While it is possible for an active ingredient to be administered alone, it is preferable to present it as a pharmaceutical formulation comprising a compound of formula (I) or a pharmacologically acceptable acid addition or base salt thereof and a pharmacologically acceptable carrier thereof. Such informations constitute a further feature of the present invention.

The formulations, both for veterinary and for human medical use, of the present invention comprise an active ingredient in association with a pharmaceutically acceptable carrier therefor and optionally other therapeutic ingredient(s). The carrier(s) must be 'acceptable' in the sense of being compatible with the other ingredients of the formulations and not deleterious to the recipient thereof.

The formulations include those in a form suitable for oral, pulmonary, ophthalmic, rectal, parenteral (including subcutaneous, intramuscular, and intravenous), intraarticular, topical, nasal, or buccal administration. Such formulations are understood to include long-acting formulations known in the art.

The formulations may conveniently be presented in unit dosage form and may be prepared by any of the methods well-known in the art of pharmacy. All methods may include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units such as capsules, cachets, tablets, or lozenges, each containing a predetermined amount of the active ingredient; in the form of a powder or granules; in the form of a solution or a suspension in an aqueous liquid or nonaqueous liquid; or in the form of an oil-in-water emulsion or a water-in-oil emulsion. The active ingredient may also be in the form of a bolus, electuary, or paste.

The usefulness of the compounds of the present invention as inhibitors of the 5-lipoxygenase enzyme, cyclooxygenase, or in treating related diseases or conditions may be demonstrated by their effectiveness in various standard test procedures A description of each procedure follows.

ARBL/ARBC Whole Cell 5-Lipoxygenase and Cyclcoxygenase Assays

Materials

The rat basophilic leukemia cell line (RBL-1) was obtained from the American Type Culture Collection (Rockville, Md.).

Radioimmunoassay (RIA) kits of $LTB_4$ and $PGF_{2\alpha}$ were obtained from Amersham (Arlington Heights, Ill.) and Seragen (Boston, Mass.), respectively All tissue culture media were obtained from GIBCO (Grand Island, N.Y.).

Method

RBL-1 cells are grown in suspension culture in Eagle's minimum essential medium supplemented with 12% fetal bovine serum at 37° C. in an incubator supplied with air-5% carbon dioxide. Cells are harvested by centrifugation. They are washed with cold phosphate buffered saline pH 7.4 (PBS; NaCl, 7.1 g; $Na_2HPO_4$, 1.15 g; $KH_2PO_4$, 0.2 g; and KCl, 0.2 g/l). Cells are finally suspended in PBS containing 1.0 mM calcium at a density of $2 \times 10^6$ cells/ml. Cells are incubated with and without test agent (in DMSO) (1% DMSO is without effect on arachidonic acid metabolism) for ten minutes at room temperature Calcium ionophore A23187 (5 $\mu$M) is added and cells are incubated for seven minutes at 37° C. The reaction is stopped by chilling the tubes on ice for ten minutes. Cells are separated by centrifugation and the supernatant is stored at $-20°$. Aliquots (100 $\mu$l) are analyzed for $LTB_4$ and $PGF_{2\alpha}$ using radioimmunoassay kits as provided by the supplier.

Table 1 contains biochemical data obtained from this whole cell assay as $IC_{50}$s which are calculated as the amount of test compound causing 50% inhibition of $LTB_4$ or $PGF_{2\alpha}$ formation.

TABLE 1

| Example | $ARBL^a$ | $ARBC$ $IC_{50}^b$ ($\mu$M) |
|---------|----------|------------------------------|
| 4       | $N^c$    | 0.51                         |

$^a$% inhibition of $LTB_4$ at 16 $\mu$M
$^b IC_{50}$ for $PGF_{2\alpha}$ inhibition
$^c$Less than 40% inhibiton Accordingly, the present invention also includes a pharmaceutical composition for treating the conditions as discussed above and a method for treating the conditions comprising administering to mammals, including humans, suffering therefrom the corresponding pharmaceutical composition. The composition contains a compound of the formula I as defined above in appropriate unit dosage form.

In addition to the compounds of formula I, the pharmaceutical compositions can also contain other active ingredients, such as cyclooxygenase inhibitors, nonsteroidal antiinflammatory drugs (NSAIDS), peripheral analgesic agents such as zomepirac, diflunisal, and the like. The weight ratio of the compound of the formula I to the second active ingredient may be varied and will depend upon the effective dose of each ingredient. Generally, an effective dose of each will be used. Thus, for example, when a compound of the formula I is combined with an NSAID, the weight ratio of the compound of the formula I to the NSAID will generally range from about 1000:1 to about 1:1000, preferably about 200:1 to about 1:200. Combinations of a compound of the formula I and other active ingredients will generally also be within the aforementioned range, but in each case, an effective dose of each active ingredient should be used.

Combinations of a compound of the formula I and other active ingredients will generally be in the aforementioned ratios.

NSAIDS can be characterized into five groups:
(1) the propionic acid derivatives;
(2) the acetic acid derivatives;
(3) the fenamic acid derivatives;
(4) the biphenylcarboxylic acid derivatives; and
(5) the oxicams or a pharmaceutically acceptable salt thereof.

The propionic acid derivatives which may be used comprise: ibuprofen, ibuprufen aluminum, indoprofen, ketoprofen, naproxen, benoxaprofen, flurbiprofen, fenoprofen, fenbufen, pirprofen, carprofen, oxaprozin, pranoprofen, miroprofen, tioxaprofen, suprofen, alminoprofen, tiaprofen, fluprofen, and bucloxic acid. Structurally related propionic acid derivatives having similar analgesic and antiinflammatory properties are also intended to be included in this group.

Thus, "propionic acid derivatives" as defined herein are nonnarcotic analgesics/nonsteroidal antiinflammatory drugs having a free $—CH(CH_3)COOH$ or $—CH_2CH_2COOH$ group (which optionally can be in the form of a pharmaceutically acceptable salt group, e.g., $—CH(CH_3)COO^-Na^+$ or $—CH_2CH_2COO^-Na^+$), typically attached directly or via a carbonyl function to a ring system, preferably to an aromatic ring system.

The acetic acid derivatives which may be used comprise indomethacin, which is a preferred NSAID, sulindac, tolmetin, zomepirac, diclofenac, fenclofenac, alclofenac, ibufenac, isoxepac, furofenac, tiopinac, zidometacin, acematacin, fentiazac, clidanac, oxpinac, and fenclozic acid. Structurally related acetic acid derivatives having similar analgesic and antiinflammatory properties are also intended to be encompassed by this group.

Thus, "acetic acid derivatives" as defined herein are nonnarcotic analgesics/nonsteroidal antiinflammatory drugs having a free —CH$_2$COOH group (which optionally can be in the form of a pharmaceutically acceptable salt group, e.g. —CH$_2$COO$^-$Na$^+$), typically attached directly to a ring system, preferably to an aromatic or heteroaromatic ring system.

The fenamic acid derivatives which may be used comprise: mefanamic acid, meclofenamic acid, flufenamic acid, niflumic acid, and tolfenamic acid. Structurally related fenamic acid derivatives having similar analgesic and antiinflammatory properties are also intended to be encompassed by this group.

Thus, "fenamic acid derivatives" as defined herein are nonnarcotic analgesics/nonsteroidal antiinflammatory drugs which contain the basic structure:

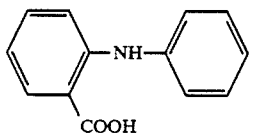

which can bear a variety of substituents and in which the free —COOH group can be in the form of a pharmaceutically acceptable salt group, e.g., —COO$^-$Na$^+$.

The biphenylcarboxylic acid derivatives which can be used comprise: diflunisal and flufenisal. Structurally related biphenylcarboxylic acid derivatives having similar analgesic and antiinflammatory properties are also intended to be encompassed by this group.

Thus, "biphenylcarboxylic acid derivatives" as defined herein are nonnarcotic analgesics/ nonsteroidal antiinflammatory drugs which contain the basic structure:

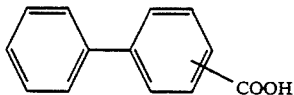

which can bear a variety of substituents and in which the free —COOH group can be in the form of a pharmaceutically acceptable salt group, e.g., —COO×Na$^+$.

The oxicams which can be used in the present invention comprise: piroxicam, sudoxicam, isoxicam, and 4-hydroxyl-1,2-benzothiazine 1,1-dioxide 4-(N-phenyl)-carboxamide. Structurally related oxicams having similar analgesic and antiinflammatory properties are also intended to be encompassed by this group.

Thus, "oxicams" as defined herein are nonnarcotic analgesics/nonsteroidal antiinflammatory drugs which have the general formula:

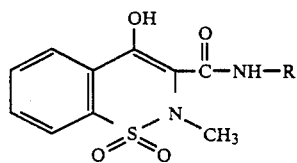

wherein R is an aryl or heteroaryl ring system.

The following NSAIDS may also be used: acemetacin, alminoprofen, amfenac sodium, aminoprofen, anitrazafen, antrafenine, auranofin, bendazac lysinate, benzydamine, beprozin, broperamole, bufezolac, carprofen, cinmetacin, ciproquazone, clidanac, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclofenac, fenclorac, fendosal, fenflumizole, fentiazac, feprazone, floctafenine, flunixin, flunoxaprofen, fluproquazone, fopirtoline, fosfosal, furcloprofen, furofenac, glucametacin, guaimesal, ibuproxam, isofezolac, isonixim, isoprofen, isoxepac, isoxicam, lefetamine HCl, leflunomide, lofemizole, lonazolac calcium, lotifazole, loxoprofen, lysin, clonixinate, meclofenamate sodium, meseclazone, microprofen, nabumetone, nictindole, nimesulide, orpanoxin, oxametacin, oxapadol, oxaprozin, perisoxal citrate, pimeprofen, pimetacin, piproxen, pirazolac, pirfenidone, pirprofen, pranoprofen, proglumetacin maleate, proquazone, pyridoxiprofen, sudoxicam, suprofen, talmetacin, talniflumate, tenoxicam, thiazolinobutazone, thielavin B, tiaprofenic acid, tiaramide HCl, tiflamizole, timegadine, tioxaprofen, tolfenamic acid, tolpadol, tryptamid, ufenamate, and zidometacin.

Finally, NSAIDS which may also be used include the salicylates, specifically aspirin, and the phenylbutazones, and pharmaceutically acceptable salts thereof.

Pharmaceutical compositions comprising the formula I compounds may also contain as the second active ingredient, antihistaminic agents such as benadryl, dramamine, histadyl, phenergan, and the like. Alternatively, they may include prostaglandin antagonists such as those disclosed in European patent application No. 11,067 or thromboxane antagonists such as those disclosed in U.S. Pat. No. 4,237,160. They may also contain histidine decarboxylase inhibitors such as α-fluoromethylhistidine, described in U.S. Pat. No. 4,325,961. The compounds of the formula I may also be advantageously combined with an H$_1$ or H$_2$-receptor antagonist, such as for instance cimetidine, ranitidine, terfenadine, famotidine, temelastine, acrivastine, loratadine, cetrizine, tazifylline, azelastine, aminothiadiazoles disclosed in EP No. 81102976.8 and like compounds, such as those disclosed in U.S. Pat. Nos. 4,283,408; 4,362,736; 4,394,508, and European patent application No. 40,696. The pharmaceutical compositions may also contain a K$^+$/H$^+$ ATPase inhibitor such as omeprazole, disclosed in U.S. Pat. No. 4,255,431, and the like. Each of the references referred to in this paragraph is hereby incorporated herein by reference.

The compound of the formula I and their salts may be prepared generally by the following processes and constitute a further aspect of the present invention.

For compounds of formula I, R$_1$, R$_2$, R$_5$, R$_6$, R$_7$ and R$_8$ are as defined above and Y is COH. Scheme I provides a method of preparation as follows:

Scheme I

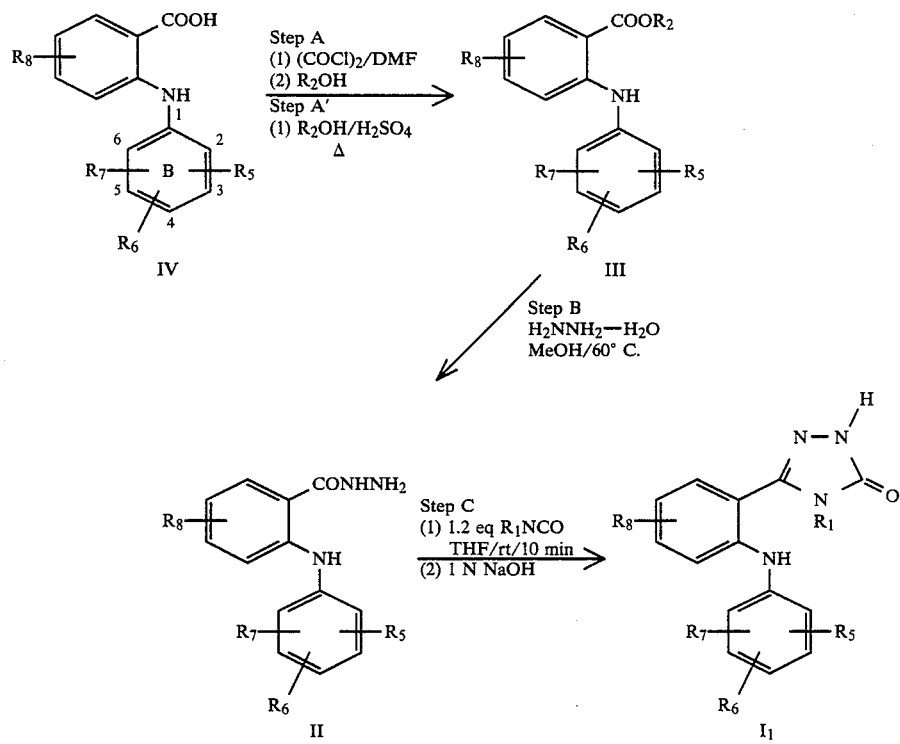

DESCRIPTION OF SCHEME I

In Step A, a fenamate of the formula IV wherein $R_5$, $R_6$, $R_7$ and $R_8$ are as defined above but in this step substituted by one of $R_5$, $R_6$ or $R_7$ other than hydrogen in each of the positions 2 and 6 of the "B" ring is treated with oxalyl chloride or thionyl chloride in tetrahydrofuran, chloroform or preferably methylene chloride that contains one drop to one equivalent of dimethylformamide. The acid chloride is added to an alcohol to give the corresponding ester of the formula III wherein $R_5$, $R_6$, $R_7$ and $R_8$ are as defined above.

Alternatively the acid of the formula IV is heated at reflux in an alcohol, preferably methanol, in the presence of sulfuric acid as shown in Step A' to give the ester of the formula III.

Esters of fenamates are known compounds and further details on their preparation can be found in P. F. Juby et al, *J. Med. Chem.*, 11, 111 (1968).

In Step B, the -ester of the formula III wherein $R_5$, $R_6$, $R_7$ and $R_8$ are as defined above in methanol or ethanol is treated with an excess of hydrazine hydrate or derivative thereof to give the hydrazide of the formula II wherein $R_5$, $R_6$, $R_7$ and $R_8$ are as defined above.

The hydrazide of the formula II can alternatively be prepared by treatment of the acid chloride which is the product of Step A 1) above with t-butyl carbazate in THF, then heating with aqueous hydrochloric acid and tetrahydrofuran.

In Step C, the hydrazide of the formula II is treated with an isocyanate, preferably methyl isocyanate, in tetrahydrofuran, followed by heating at reflux with aqueous sodium hydroxide to give the N-methyl triazolone of the formula $I_1$ wherein $R_1$, $R_5$, $R_6$, $R_7$ and $R_8$ are as defined above.

For compounds of formula I wherein $R_1$, $R_2$, $R_5$, $R_6$, $R_7$ and $R_8$ are as defined above; and Y is CSH. Scheme II provides a method of preparation as follows:

Scheme II

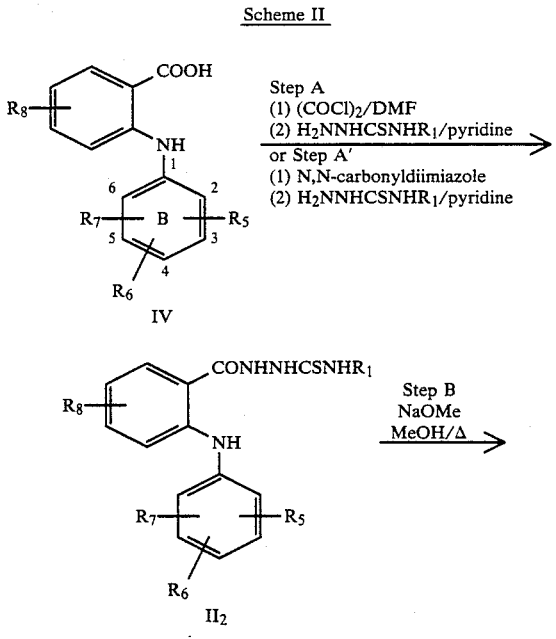

-continued
Scheme II

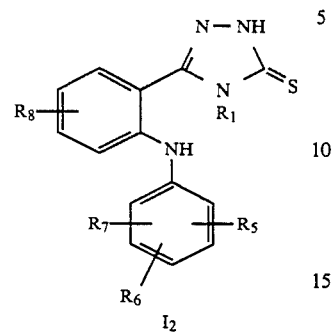

DESCRIPTION OF SCHEME II

In like manner in Step A, the aforesaid acid chloride which is the product of Scheme I or II Step A (1) is treated with thiosemicarbazide of the formula H$_2$NNH$_1$CSNHR$_1$ wherein R$_1$ is as defined above, in dioxane, tetrahydrofuran, methylene chloride or preferably pyridine to give the hydrazide thioamide of the formula II$_2$ wherein R$_1$, R$_5$, R$_6$, R$_7$ and R$_8$ are as defined above.

Alternatively the acid of formula IV is treated with N,N'-carbonyldiimidazole to give an imidazolide. This intermediate is treated with thiosemicarbazide in refluxing pyridine to give the hydrazide thioamide of the formula II$_2$ wherein R$_1$, R$_5$, R$_6$, R$_7$ and R$_8$ are as defined above.

In Step B, the product of Step A of the formula II$_2$ is dissolved in methanol or ethanol and treated with sodium methoxide or sodium ethoxide (generated from sodium and ethanol) or an organic base such as pyridine or preferably piperdine. The mixture is heated at reflux to give the triazole thione of the formula I$_2$ wherein R$_1$, R$_5$, R$_6$, R$_7$ and R$_8$ are as defined above.

Aminotriazole 2 may be prepared by treating acid chloride 1 with aminoguanidine bicarbonate in refluxing toluene with removal of H$_2$O using a Dean-Stark trap or molecular sieves; Scheme III below.

Scheme III

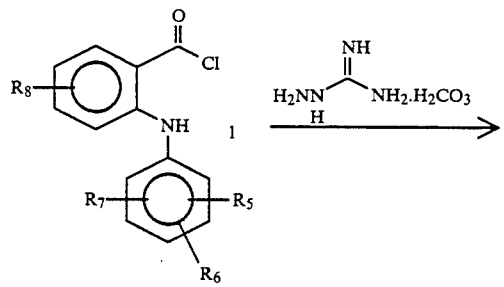

-continued
Scheme III

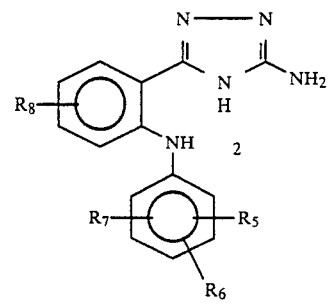

Scheme IV below provides methods for the conversion of compounds of type 1 wherein Y is C-SH to compounds of type 1 wherein Y is C—SOR$_2$, C—SO$_2$R$_2$, C—OR$_1$, CNR$_1$R$_3$, or C—NHCN. The conversion of Y is C—OH to Y is C—OR$_2$ is also shown in Scheme IV.

Scheme IV

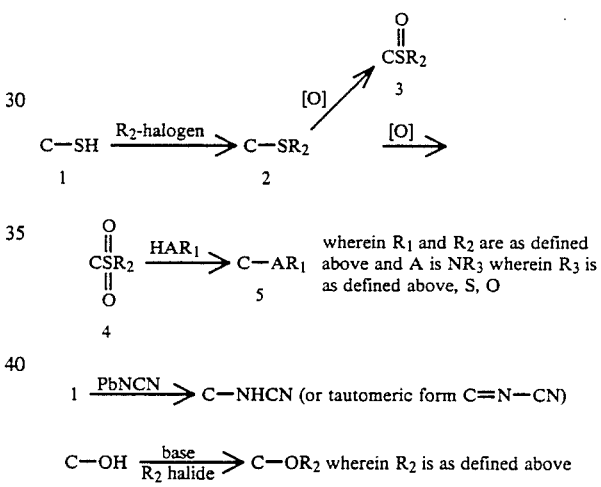

Scheme IV indicates various transformations of Y.

Treatment of compounds of type 1, wherein Y is C—SH with bases such as KH, NaH, or t-BuOK in the presence of R$_2$halogen, where R$_2$=H or alkyl, using a protic solvent such as diethyl ether, tetrahydrofuran, or dimethylformamide, gives compounds of type 2. Treatment of 2 with an oxidizing agent such as KMnO$_4$, H$_2$O$_2$ in acetic acid or m-chloroperbenzoic acid, (MCPBA) gives sulfones of type 4. Treatment of 4 with HAR' in the presence or absence of a base where A is O, S, or NR$_3$ to give compound 5. Treatment of 2 with 1 equivalent of MCPBA, H$_2$O$_2$ or NaIO$_4$ gives 3.

When compounds where Y is C—OH are treated with alkylhalides (R$_2$X) in the presence of a base such as NaH, NaOH, KOH, KH, LiOH, t-BuOK, or triethylamine, then the resulting products are ethers.

Scheme V below provides methods for the conversion of compounds of type 1 wherein Y is C—NH$_2$ to compounds of type 1 wherein Y is C—OR$_1$, C—SR$_1$, C—Halogen, C—NHSO$_2$R$_2$, C—NHCONHR$_1$, and C—NHCSNHR$_1$.

Scheme V

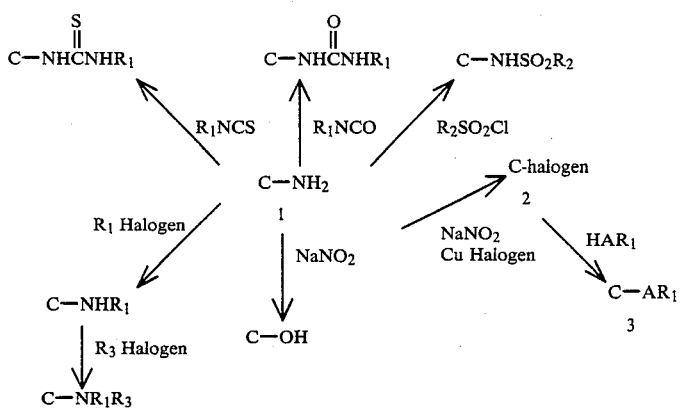

wherein $R_1$, $R_2$, and $R_3$ are as defined above.

The transformations shown in Scheme V are standard synthetic reactions. For example, $\underline{1}$ (Y=C—NH$_2$) is treated with NaNO$_2$, Cu halogen and H halogen (Sandmeyer reaction conditions) to give $\underline{2}$ (Y=C—Cl). Treatment of $\underline{2}$ with HAR$_1$ (A is O, S or R$_3$) gives $\underline{3}$ (Y=C—AR$_1$)

One of skill in the art would recognize variations in the sequence and would recognize appropriate reaction conditions from analogous reactions which may be appropriately used in the processes to make the compound of formula (I) herein. Further, the starting materials are known or can be prepared by known methods.

Under certain circumstances as discussed above, it is necessary to protect either the N or O of intermediates. The examples above showing this noted process with suitable protecting groups which are known are not meant to be limiting. Introduction and removal of such suitable oxygen and nitrogen protecting groups are well-known in the art of organic chemistry; see for example "Protective Groups in Organic Chemistry," J. F. W. McOmie, *Advances in Organic Chemistry*, Vol. 3, 191–281 (1963); R. A. Borssonas, *Advances in Organic Chemistry*, Vol. 3, 159–190 (1963); J. F. W. McOmie, *Chem. & Ind.*, 603 (1979), and T. W. Greene, "Protective Groups in Organic Synthesis", Wiley (New York) 1981, Chapters 2, 3, and 7.

Examples of suitable oxygen protecting groups are benzyl, t-butyldimethylsilyl, ethoxyethyl, methoxyethoxymethyl, and the like. Protection of an N-H containing moiety is necessary for some of the processes described herein for the preparation of compounds of this invention. Suitable nitrogen protecting groups are benzyl, triphenylmethyl, trialkylsilyl, trichloroethylcarbamate, trichloroethoxycarbony, vinyloxycarbamate acetyl, and the like.

Under certain circumstances it is necessary to protect two different oxygens with dissimilar protecting groups such that one can be selectively removed while leaving the other in place. The benzyl and t-butyldimethylsilyl groups are used in this way; either is removable in the presence of the other, benzyl being removed by catalytic hydrogenolysis, and t-butyldimethylsilyl being removed by reaction with, for example, tetra-n-butylammonium fluoride.

In the process described herein for the preparation of compounds of this invention the requirements for protective groups are generally well recognized by one skilled in the art of organic chemistry, and accordingly the use of appropriate protecting groups is necessarily implied by the processes of the charts herein, although not expressly illustrated.

The products of the reactions described herein are isolated by conventional means such as extraction, distillation, chromatography,-and the like.

The invention is further elaborated by the representative examples as follows. Such examples are not meant to be limiting.

PREPARATION 1

Methyl 2-[(2,6-dichloro-3-methylphenyl)amino]-benzoate

Oxalyl chloride (9.50 g, 74.8 mmol) in 20 ml of methylene chloride is added dropwise to a 0° C. suspension of 2-[(2,6-dichloro-3-methylphenyl)amino]benzoic acid (10.20 g, 34.4 mmol) and dimethylformamide (2.70 ml, 34.7 mmol) in 50 ml of methylene chloride. The clear yellow solution is stirred at 0° C. for 90 minutes then added by cannula to 110 ml of methanol at room temperature. The white suspension is stirred at room temperature overnight. The white solid is collected providing 7.52 g of product. The filtrate is concentrated and the residue partitioned between ethyl acetate and water. The organic layer is washed with brine, dried over magnesium sulfate and concentrated, providing an additional 2.45 g of methyl 2-[(2,6-dichloro-3-methylphenyl)amino]-benzoate (94% total), mp 130°–131° C.

Anal. for $C_{15}H_{13}Cl_2NO_2$ requires: C, 58.08; H, 4.22; Cl, 22.86; N, 4.52. Found: C, 57.72; H, 4.13; Cl, 22.99; N, 4.38.

PREPARATION 2

2-[(2,6-Dichloro-3-methylphenyl)amino]-benzoic acid, hydrazide

Hydrazine hydrate (2 ml) is added dropwise to a suspension of methyl 2-[(2,6-dichloro-3-methylphenyl)amino]benzoate (227.1 mg, 0.73 mmol) in 10 ml of methanol. The reaction mixture is heated at 60° C. for seven hours under an atmosphere of nitrogen and then allowed to cool to room temperature overnight. The now clear colorless solution is concentrated in vacuo and chromatographed, eluting with ethyl acetate and hexane (gradient of 1:2 to 1:1), providing 208.6 mg (92%) of a white solid, mp 158°–160° C.

Anal for $C_{14}H_{13}Cl_2N_3O$ requires: C, 54.21; H, 4.22; Cl, 22.86; N, 13.55. Found: C, 54.16; H, 4.20; Cl, 22.95; N, 13.44.

EXAMPLE 1

5-[2-[2,6-Dichloro-3-methylphenyl)amino]phenyl]-2,4-dihydro-4-methyl-3H-1,2,4-triazol-3-one Methyl isocyanate (190 μl, 3.22 mmol) is added dropwise to a room temperature solution of 2-[(2,6-dichloro-3-methylphenyl)amino]-benzoic acid, hydrazide (888.6 mg, 2.86 mmol) in 11 ml of methanol. After stirring at room temperature for 15 minutes, 100 ml of ether is added and the white solids removed by filtration, washing with ether. The white solid is dried to give 909.9 mg (87%) of product, that is not purified A portion (862.6 mg, 2.35 mmol) is suspended in 3 ml of water and treated with 3 ml of 1N sodium hydroxide solution. The resultant orange solution is heated at reflux overnight. An additional 2 ml of sodium hydroxide is added and reflux is resumed overnight. The mixture is cooled to room temperature and the liquid is decanted off and acidified with 1N hydrochloric acid. The white solids are removed by filtration, washing with water. Flash chromatography eluting with hexane:ethyl acetate (2:1) gave 267.8 mg (33%) of 5-[2-[(2,6-dichloro-3-methyl-phenyl) amino]phenyl]-2,4-dihydro-4-methyl-3H-1,2,4-triazol-3-one, mp 280°-285° C. dec.

Anal. for $C_{16}H_{14}Cl_2N_4O$ requires: C, 55.03; H, 4.04; N, 16.04. Found: C, 55.02; H, 4.05; N, 15.69.

PREPARATION 3

2-[(2,6-dichloro-3-methylphenyl)amino]-benzoic acid, 2-(aminothioxomethyl)hydrazide Oxalyl chloride (2.85 g, 22.5 mmol) in 10 ml of methylene chloride is added dropwise to a 0° C. suspension of 2-[(2,6-dichloro-3-methylphenyl)amino]-benzoic acid (3.17 g, 10.6 mmol) and dimethylformamide (830 μl, 10.6 mmol) in 50 ml of methylene chloride. The clear yellow solution is stirred at 0° C. for 15 minutes and then at room temperature for 30 minutes. The solution is then concentrated in vacuo to give a yellow solid. This solid is added in portions to a suspension of thiosemicarbazide (1.95 g, 21.4 mmol) in 20 ml of pyridine. The suspension is stirred at 0° C. for 30 minutes then at room temperature overnight. The reaction mixture is concentrated in vacuo and the residue is partitioned between ethyl acetate and water. The organic layer is concentrated, then slurried with equal volumes of ethyl acetate and hexane. The off-white solid is collected by filtration providing 1.66 g (42%) of 2-[(2,6-dichloro-3-methyl-phenyl)amino]-benzoic acid, 2-(aminothioxomethyl)hydrazide, mp is undefined.

Anal. for $C_{15}H_{14}Cl_2N_4SO$ requires: C, 48.79; H, 3.82; N, 15.17; S, 8.68. Found: C, 48.39; H, 3.74; N, 15.45; S, 8.37.

EXAMPLE 2

5-[2-[(2,6-Dichloro-3-methylphenyl)amino]phenyl]-2,4-dihydro-3H-1,2,4-triazole-3-thione Sodium methoxide (734.0 mg, 13.59 mmol) is added to a solution of 2-[(2,6-dichloro-3-methylphenyl)amino]-benzoic acid, 2-(aminothioxomethyl)-hydrazide (1.466 g, 3.96 mmol) in 60 ml of methanol and the mixture is heated at reflux overnight, under a nitrogen atmosphere. An additional amount of sodium methoxide (702.0 mg, 13.00 mmol) is added and heating at reflux is continued overnight. The volatiles are removed in vacuo and the residue dissolved in water. The aqueous solution is acidified to pH 4-5 with 10% hydrochloric acid. The resultant white solid is collected, dissolved in tetrahydrofuran and chromatographed, eluting with hexane:ethyl acetate (1:2) to give 599.2 mg (43%) of 5-[2-[(2,6-dichloro-3-methylphenyl)amino]phenyl]-2,4-dihydro-3H-1,2,4-triazole-3-thione, mp 300°-305° C.

Anal. for $C_{15}H_{12}Cl_2N_4S$ requires: C, 51.29; H, 3.44; Cl, 20.19; N, 15.95; S, 9.13. Found: C, 51.38; H, 3.57; Cl, 19.93; N, 15.78; S, 9.11.

PREPARATION 4

2-[(3-trifluoromethylphenyl)amino]-benzoic acid, 2-(aminothioxomethyl)hydrazide

N,N'-Carbonyldiimidazole (4.56 g, 27.6 mmol) is added to a room temperature solution of flufenamic acid (5.07 g, 18.0 mmol) in 70 ml of tetrahydrofuran. The clear yellow solution is stirred at room temperature for three hours. The solution is then added via cannula to a suspension of thiosemicarbazide (3.41 g, 37.5 mmol) in 55 ml of pyridine. The suspension is heated at reflux overnight. The clear orange solution is concentrated in vacuo and the residue is partitioned between ethyl acetate and water. The organic layer is washed with water, dried over magnesium sulfate and concentrated. The resulting solid is slurried with a 1:3 mixture of ethyl acetate and hexane. The off-white solid is collected by filtration providing 2.80 g (44%) of 2-[(3-trifluoromethylphenyl)amino]-benzoic acid, 2-(aminothioxomethyl)hydrazide.

EXAMPLE 3

5-[2-[(3-trifluoromethylphenyl)amino]phenyl]-2,4-dihydro-4-methyl-3H-1,2,4-triazol-3-one Methyl isocyanate (230 μl, 3.89 mmol) is added dropwise to a room temperature solution of 2-[(3-trifluoromethylphenyl)amino]-benzoic acid, hydrazide (1.003 g, 3.49 mmol) in 15 ml of tetrahydrofuran. After stirring at room temperature for 10 minutes, 100 ml of hexane is added. After 1.5 hours the white solids are removed by filtration, washing with hexane. The solid is dried to give 1.115 g (82%) of product, that is not purified.

A portion (996.5 mg, 2.83 mmol) of the above material is suspended in 4 ml of water and treated with 6.2 ml of 1N sodium hydroxide solution The resultant solution is heated at reflux for two days. The mixture is cooled to room temperature and acidified with 1N hydrochloric acid. The white solids are removed by filtration, washing with water. Flash chromatography eluting with hexane:ethyl acetate (1:1) gives 448.1 mg (47%) of 5-[2-[(3-trifluoromethylphenyl) amino]phenyl]-2,4-dihydro-4-methyl-3H-1,2,4-triazol-3-one, mp 178°-180° C.

Anal for $C_{16}H_{13}F_3N_4O$ requires: C, 57.48; H, 3.92; F, 17.05; N, 16.76. Found: C, 57.62; H, 3.80; F, 17.13; N, 16.42.

EXAMPLE 4

5-[2-[3-(trifluoromethylphenyl)amino]phenyl]-2,4-dihydro-3H-1,2,4-triazole-3-thione Sodium methoxide (548.0 mg, 10.5 mmol) is added to a solution of 2-[(3-trifluoromethylphenyl)amino]-benzoic acid, 2-(aminothioxomethyl)hydrazide (1.023 g, 2.89 mmol) in 50 ml of methanol and the mixture is heated at reflux under a nitrogen atmosphere. Additional amounts of sodium methoxide (548.0 mg and 250.0 mg) are added after heating at reflux for one and two days. The volatiles are removed in vacuo and the residue dissolved in water. The aqueous solution is acidified to pH 4–5 with 1N hydrochloric acid. The resultant pale yellow solid is collected to give 934.1 mg. The solid is chromatographed, eluting with hexane:ethyl acetate (1:2) to give 580.0 mg (59%) of 5-[2-[(3-trifluoromethylphenyl)amino]phenyl]-2,4-dihydro-3H-1,2,4-triazole-3-thione, mp 275°–279° C.

Anal. for $C_{15}H_{11}F_3N_4S$ requires: C, 53.56; H, 3.30; N, 16.66; S, 9.53. Found: C, 53.65; H, 3.05; N, 16.37; S, 9.71.

I claim:

1. A compound of the formula (I)

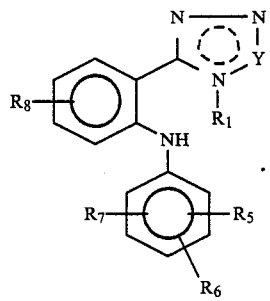

and a pharmaceutically acceptable salt thereof; wherein
$R_1$ is hydrogen or lower alkyl;
Y is (1) C—$SR_1$ wherein $R_1$ is H or lower alkyl (2)

wherein $R_2$ is lower alkyl, (3)

wherein $R_2$ is as independently defined above, (4) C—$NR_1R_3$ wherein $R_1$ is independently as defined above and $R_3$ is hydrogen or lower alkyl, (5) $COR_1$ wherein $R_1$ is independently as defined above, (6) $CR_4$ wherein $R_4$ is hydrogen, lower alkyl,-halogen, $CF_3$, $CO_2R_1$, or

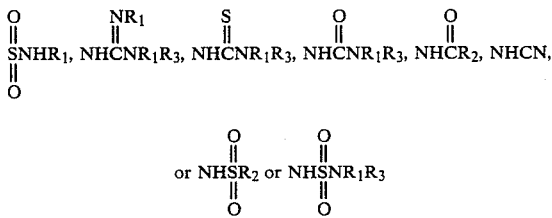

wherein $R_1$, $R_2$, and $R_3$ are independently as defined above; and $R_5$, $R_6$, $R_7$, and $R_8$ are independently hydrogen, fluoro, chloro, bromo, iodo, trifluoromethyl, lower alkyl, CN, hydroxy, lower alkoxy, —$S(O)_n$-lower alkyl, $NO_2$, or $NR_9R_{10}$ wherein $R_9$ or $R_{10}$ are independently H, lower alkyl or lower alkanol; and n is an integer of 0 through 2.

2. A compound of claim 1 wherein Y is COH.
3. A compound of claim 1 wherein Y is CSH.
4. A compound of claim 2 which is 5-[2-[2,6-dichloro-3-methylphenyl)amino]phenyl]-2,4-dihydro-4-methyl-3H-1,2,4-triazol-3-one.
5. A compound of claim 2 which is 5-[2-[(3-trifluoromethylphenyl)amino]phenyl]-2,4-dihydro-4-methyl-3H-1,2,4-triazol-3-one.
6. A compound of claim 3 which is 5-[2-[(2,6-dichloro-3-methylphenyl)amino]phenyl]-2,4-dihydro-3H-1,2,4-triazole-3-thione.
7. A compound of claim 3 which is 5-[2-[(3-trifluoromethylphenyl)amino]phenyl]-2,4-dihydro-3H-1,2,4-triazole-3-thione.
8. A pharmaceutical composition for use as an antiinflammatory agent comprising an antiinflammatory amount of the compound of claim 1 and a pharmaceutical carrier.
9. A method of treating inflammation in a mammal suffering therefrom which comprises administering the compound of claim 1 in unit dosage form.

* * * * *